United States Patent [19]

Killeen et al.

[11] Patent Number: 5,166,051

[45] Date of Patent: Nov. 24, 1992

[54] MEMBRANES, MEMBRANE OVERLAYS FOR EXCLUSION OF ERYTHROCYTES, AND METHOD FOR IMMUNOASSAY OF WHOLE BLOOD ANALYTES

[75] Inventors: Yvonne M. Killeen, St. Paul; Ernest C. Adams, Eden Prairie; Karen R. Mason, Edina, all of Minn.

[73] Assignee: Genesis Labs, Inc., Minneapolis, Minn.

[21] Appl. No.: 564,631

[22] Filed: Aug. 8, 1990

[51] Int. Cl.[5] .......................... G01N 33/543
[52] U.S. Cl. .......................... 435/7.1; 422/55; 422/56; 422/57; 422/58; 422/61; 435/969; 435/970; 435/975; 436/521; 436/531; 436/169; 436/170; 436/805
[58] Field of Search .................. 422/55-58, 422/61; 435/7.1, 969, 970, 975; 436/521, 531, 169, 170, 805

[56] References Cited

U.S. PATENT DOCUMENTS

| | | | |
|---|---|---|---|
| 4,186,251 | 1/1980 | Tarbutton | 435/11 |
| 4,362,697 | 12/1982 | Tabb et al. | 435/805 |
| 4,446,232 | 5/1984 | Liotta | 435/7 |
| 4,668,472 | 5/1987 | Sakamoto et al. | 422/56 |
| 4,710,458 | 12/1987 | Maines | 435/12 |
| 4,839,296 | 6/1989 | Kennedy et al. | 436/170 |
| 4,839,297 | 6/1989 | Freitag et al. | 436/170 |
| 4,939,096 | 6/1990 | Tonelli | 436/541 |
| 4,994,238 | 2/1991 | Daffern et al. | 422/57 |

Primary Examiner—Robert J. Hill, Jr.
Assistant Examiner—Christopher L. Chin
Attorney, Agent, or Firm—Merchant, Gould, Smith, Edell, Welter & Schmidt

[57] ABSTRACT

A diagnostic test strip for chemically determining whole blood analytes comprises a support, a porous detection zone membrane affixed to the support, and an overlay membrane affixed to the support and in overlying and continuous contact with the detection zone membrane. The overlay membrane has a crenating agent for the exclusion of whole red blood cells from the pores of the detection zone membrane.

20 Claims, 2 Drawing Sheets

MEMBRANES, MEMBRANE OVERLAYS FOR EXCLUSION OF ERYTHROCYTES, AND METHOD FOR IMMUNOASSAY OF WHOLE BLOOD ANALYTES

FIELD OF THE INVENTION

The present invention relates to a testing system for the chemical or immunological assay of whole blood analytes. More specifically, the present invention relates to a diagnostic test strip system comprising an overlay membrane containing a crenating agent and a detection membrane with pores which prevent penetration of erythrocytes into the analyte determining detection zone of the test strip system.

BACKGROUND OF THE INVENTION

The determination of whole blood analytes is an established diagnostic tool in the medical and health care industries. One problem encountered in the determination of whole blood analytes is the penetration or permeation of red blood cells (RBC) into the reactive, analyte determining sites in the testing system. A major cause of immuno assay or chemical assay interference in the detection of a signal from an analyte detection zone arises from RBC in the test fluid. As the test fluid contacts an absorbent detection zone on a membrane carrier, the RBC along with the other components of the test fluid are absorbed into and penetrate through the membrane and become intermingled in the detection zone. The presence of whole RBC in the detection zone results in a discoloration which physically and chemically interferes with colorimetric assay procedures.

A red blood cell is known to comprise an outer membrane enclosing a solution that is high in concentration of hemoglobin. The red blood cell and the free hemoglobin from hemolysis of the cell can impart a color to the detection zone ranging from light pink to dark maroon. As a consequence, the production of a visual chemical signal can be partially or wholly obscured by the presence of the hemoglobin color in the detection zone. Furthermore, the hemoglobin can block the production of electromagnetic radiation in a fluorescent-type signal generating indicator system. The rapidity of use, accuracy and precision of the dry test strip in the qualitative or quantitative analysis of analytes can be seriously inhibited by the presence of RBC, hemoglobin and other contents of the red blood cell in the detection zone or layer.

Various techniques have been developed to eliminate the physical and chemical interferences created by the presence of whole RBC in the detection zones. One alternative, has been the physical elimination of the RBC from the sample. Specifically, centrifuge techniques have been used to spin down samples thereby expediting the removal of RBC from the samples. Agglutinating agents have also been used to clump RBC and facilitate physical collection and removal of whole RBC from a sample. Alternatively, autonomous or spray applied size exclusion membranes having a definite pore size have been used to create and allow analyte penetration of the detection zone but exclude whole RBC from the detection zone membrane.

However, the use of size exclusion processes does not completely eliminate interferences created by the presence of RBC at the detection zones. A red blood cell can squeeze through a pore having a smaller relative diameter than that of the red blood cell due to the malleable or flexible character of the cell. Furthermore, the use of smaller pores reduces the real volume of analyte which is allowed to pass through any size exclusive membrane and actually contact the detection zone. Consequently, the reduced flow of analyte to the detection zone may result in variable assay results which prove to be undependable in any given instance.

Accordingly, a need exists for a test system for determining select analytes in whole blood samples which is unaffected by the chemical or physical interferences normally created by RBC.

SUMMARY OF THE INVENTION

The present invention comprises a diagnostic test strip for the chemical or immunological assay of whole blood analytes comprising a support, a porous detection zone membrane affixed onto the support, and an overlay membrane affixed to the support and in overlying and continuous contact with the detection zone membrane. The overlay membrane contains an effective amount of a crenating agent for the exclusion of whole red blood cells or erythrocytes from the pores of the detection zone membrane.

The detection zone membrane contains a chemical or immuno assay that can generate a characteristic signal in the presence of a target analyte. The overlay membrane lying in continuous contact with the detection zone membrane prevents the passage of RBC through the pores of the detection zone membrane through the presence of the crenating agent. The red blood cells in passing through the overlay membrane are crenated and made rigid and are thereby excluded by the pores of the detection zone membrane.

Another aspect of the invention is directed to a method of using the diagnostic test strip for determining the presence of a target analyte in whole blood.

DETAILED DESCRIPTION OF THE INVENTION

Figure 1:
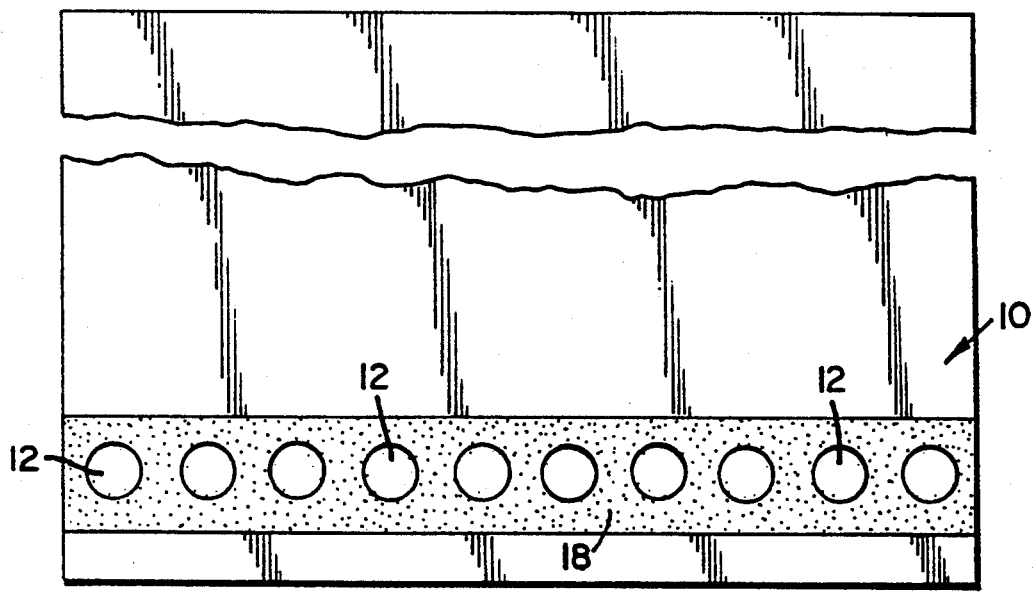
FIG. 1 depicts a planar view of the support having reading sites and an adhesive strip overlay used to make the test strips of the invention.

The diagnostic test strip of the present invention for the chemical or immunological assay of whole blood analytes comprises a base or substrate, a porous detection zone membrane affixed to the substrate and containing a reagent system that can generate a detectable signal in the presence of an analyte target, and an overlay membrane affixed to the substrate and in overlying and continuous contact with the detection zone membrane. The detection zone membrane is protected from red blood cell interference in the visualization of a signal by the combination of the overlay membrane and the pores of the detection membrane.

SUPPORT

The base or support of the present invention functions to hold the test strip system and provides a handle. The support also provides a basis for further mounting of the test strip to make any of a variety of testing products.

Generally, any type of natural or synthetic material which provides the necessary rigidity and inertness prior to the use of the test system and upon exposure to the fluid analyte may be used as a support. The support can be of a variety of shapes and forms, having varied dimensions depending on the applicability of the material in production. The support typically will have a thickness of at least 0.1 micron, typically greater than 1 micron, generally in the range of 10 to 100 microns. The support can be opaque, translucent or transparent. However, the signal generated by the detection zone should not be masked by the nature of the support.

Various materials can be employed in the support which avoid interfering with signal generation, allow passage of the test fluid, and allow reaction of the test components. A wide variety of organic and inorganic polymers, both natural and synthetic, may be employed in the support including polyethylene, polyvinyl chloride, polypropylene, poly-4-methylbutene, polystyrene, polymethacrylate, polyethylene terephthalate, rayon, nylon, polyvinyl butyrate, silicone films, polyformaldehyde, cellulose, cellulose acetate, nitrocellulose, etc. A preferred polymer for the support of the invention is polystyrene. Other materials which may be used include paper, glass, fiberglass, ceramics, metals, metal foils, metalloids, semi-conductive materials, and others. Additionally, natural substances that can form gels or films including proteins or protein derivatives, cellulosics, drying oils, and others can be used to form the support. The support material is preferably nonswellable, and mildly hydrophilic.

DETECTION ZONE MEMBRANE

The detection zone membrane of the present invention provides a reactive detection system for the identification of any chosen analyte. These reactive membranes can be made of a variety of synthetic and natural porous polymeric materials that are permeable to the analyte. A primary function of the materials making up the detection zone membrane is to act as a site or locus for an effective concentration of the detection zone components and to provide an effective flow of the test fluid through the detection zone to permit reaction between the analyte and the immunoassay or chemical assay reagents contained within the test device. The detection zone membrane can be of a variety of shapes and forms having varied dimensions. The typical membrane material will have a thickness of at least 0.1 mil (1 mil equals 0.001 inch), typically greater than 1 mil, generally in the range of 10-30 mil. These materials can be semi-opaque, translucent or transparent. However, the signal generated by the immuno or chemical assay should not be masked by the nature of the membrane material.

A preferred material for forming the reactive detection zone membrane comprises a porous nylon membrane formed by casting a porous nylon sheet on a nonwoven layer (e.g., polyester). Biodyne and Immunodyne from Pall are examples of this preferred material. Such a membrane provides uniform pore size (minimum of 0.04 micron, preferably 0.2 to 3 microns), chemical inertness to typical solvents and reagents used in forming dry test strips, and provides significant mechanical strength and integrity that promotes rapid and accurate production. The Immunodyne membrane has reactive groups or sites which are used to bind an amine, such as polyallylamine, which can be reacted with the membrane to give a charge to the membrane. The charge aids in preventing the blood cells from passing into the pores of the detection zone membrane.

The detection zone membrane also comprises an activated colorimetric indicator for determining a select analyte constituent in the whole blood. The signal which is generated by the indicator in the detection zone membrane indicates both presence and concentration of a target analyte. Generally any readily available indicator which is adequate for determining a chosen analyte and that is compatible with a dry test strip format may be used in the detection zone membrane. Preferred indicators include glucose and cholesterol indicators.

The detection zone membrane preferably additionally comprises analyte reactive precursors that modify whole blood analytes to provide a constituent determinable by the detection zone membrane. The analyte reactive precursors preferably comprise cholesterol ester hydrolase and cholesterol oxidase when cholesterol is the desired target analyte. The analyte reactive precursors preferably comprise glucose oxidase and peroxidase when glucose is the target analyte.

The detection zone membrane may also contain additional constituents and materials such as buffers including, for example, morpholino-ethanesulfonic acid (MES), citrate, citrate/acetate combinations, bishydroxyethylglycine, or other buffers all of which may be used to buffer the detection zone membrane to a range appropriate for determination of a chosen analyte. The detection zone membrane may also contain wetting agents, such as nonionic or anionic surfactants or blood thinners such as heparin which may be used to increase the flow of analyte to the detection zone.

The detection zone membrane needs to be made in a buffer solution having a pH of about 5 to 7 with a pH of 6 being preferred. When the pH is too high, the membrane is not effective in blocking blood cells and when the pH is too low the amine functionality of polyallylamine will not attach to the reactive sites to generate a charge in the membrane.

A reactive cholesterol detection zone membrane can be prepared by the following method. First a membrane with reactive sites (such as Pall's Immunodyne R) is reacted with polyallylamine and then with a dried milk preparation to give a charged membrane. The washed and dried membrane is then impregnated with an aqueous mixture containing the enzymes cholesterol oxidase, cholesterol esterase (or lipase) and peroxidase, a buffer, surfactant, heparin, etc., and then dried. The membrane is then impregnated with an organic solvent solution of the indicator (such as orthotolidine or tetramethylbenzidine), a surfactant, and potentiators. A considerable quantity of red blood cells is screened out by this membrane treatment, but enough cells get through to still give a red background, to inhibit the reaction and to obscure the pure blue color (if tetramethylbenzidine is the indicator). A glucose detection zone membrane may also be prepared by the above method except for the inclusion of the enzyme glucose oxidase instead of the cholesterol enzymes.

OVERLAY MEMBRANE

The overlay membrane generally comprises a porous membrane of varying thickness containing a crenating agent. The crenating agent functions to deplete the volume of fluid within the red blood cell. Once the cell becomes crenated or has been shrunk, it is much less malleable and flexible and becomes rigid. The overlay membrane should allow for passage of the analyte once it has been released from the solution of whole red blood cells. Preferably the overlay membrane does not have defined pores, but has intermatted fibers.

Optionally, the overlay membrane may be hydrophilic on one side and hydrophobic on the other to prevent the reverse flow of analyte away from the direction of the detection zone membrane. The overlay membrane must remain in continuous contact over the entire surface of the detection zone membrane to provide a uniform size exclusion of RBC as well as to provide a uniform and continuous channel for the analyte to flow from the upper surface of the overlay membrane to the detection zone membrane.

The overlay membrane can be made from a synthetic polymeric material and has a thickness of about 0.1 to 1,000 microns. While any number of overlay membranes may generally be used in the present invention, high density polypropylene membranes manufactured under the brand name of HDC polypropylene by Pall, Inc., polyvinyl chloride membranes manufactured by Labconco, polyester membranes manufactured by DuPont and polypropylene non-woven membranes treated with various wetting agents or surfactants have all been found useful in the present invention.

The crenating agent in the overlay membrane functions to shrink RBC by extracting fluid from the cells. The shrinking or volume depleting action of the crenating agent rigidifies the cells making them less flexible and malleable and in turn, less able to penetrate into the pores of the detection zone membrane. As a result, the stiffer, less flexible cells cannot move easily into the pores and are trapped at the surface of the detection membrane. In the meantime, the liquid analyte compositions flow through the overlay membrane and penetrate the detection zone membrane to provide for a viable signal.

Generally, the crenating agent may be any constituent or composition which effectively reduces the volume of water within the RBC flowing through the overlay membrane. Particularly useful are inorganic and organic salts which, when present in greater than hypertonic concentration, draw water from the interior of the RBC. Inorganic salts are preferred, such as the alkali or alkali earth metal salts of a halogen, or any salt of a strong acid or base. These salts can include sulfates, nitrates, and chlorides, such as sodium chloride, lithium chloride, and potassium chloride. The above salts are all useful as they remain outside the cell wall, do not interfere with the indicator or analyte and are readily available as staple chemicals. A particularly preferred inorganic salt for use in the present invention is sodium chloride.

Generally, the concentration of the salt solution used to treat the overlay membrane will range at a level exceeding that which would be hypertonic and soluble. For sodium chloride the concentration should be from about 0.85 to about 35%, preferably from about 1 to about 10% and most preferably from about 2 to about 6%. As the most preferred concentration of crenating agent is that concentration which is by definition hypertonic, the concentration will vary depending upon the crenating agent of choice. Accordingly, these concentration ranges should be used as guidelines and not be strictly interpreted as limitations on the usefulness of the present invention.

ANALYTES

Virtually any analyte detectable using an immunological or chemical assay system can be detected using the test strip system of the present invention. A high molecular weight analyte detected by the device of this invention is characterized as typically large molecule polypeptides, polysaccharides, polynucleic acids and combinations thereof. Other analytes can include somatic cells, germ cells, bacteria, viruses and cellular units.

Subcellular units which can be analytes include viral protein, cell wall polysaccharides, DNA, DNA segments, RNA, transfer RNA, messenger RNA, mitochondrial DNA, mitochondrial cell nuclei, cell membranes, ribosomes, and other varied cell organelles, subunits and constituent parts. Such large analytes are typically detected using immunological dry test strips of the invention and can have molecular weights in excess of about 50,000. Many such analytes can have molecular weights ranging from 50,000 to 5,000,000 or more.

The analytical test strips of the present invention can also be used to detect and quantitate the presence of analytes having modest molecular weights, i.e., molecules with a molecular weight less than about 50,000, typically between 5,000 and 50,000. A wide variety of such analytes that comprise natural proteins and protein subunits can be detected using the device of the invention. Such proteins include histones, globulins, nucleoproteins, lipoproteins, glycoproteins, somatotropin, prolactin, insulin, pepsin, human plasma protein constituents including human albumin, thyroxine, binding globulins, haptoglobulin, cerulo plasmin, cholinesterase, myoglobin, fibrinogen, plasminogen, poly and monoclonol immunoglobulins of the A, D, E, G, or M classes, free, light or heavy chains of amino globulens, Fab fragment or $F(ab')_2$ fragment, immuno globulin regions, compliment, blood clotting factors, peptide and protein hormones such luteinizing hormone, human chorionic gonadotropin, vasopressin, and others. Such proteins are typically detected using a immunological detection scheme. Antigenic polysaccharides derived from pathogen cell walls also act as an immunological antigen.

Further, small molecules of natural and synthetic origin can also be detected using the dry test strips of the invention. Such small molecules having a molecular weight of about 50 to 5,000, typically 100 to 2,000 can be detected using both chemical and immunological detection schemes. Such analytes include small molecule natural biochemicals, ethical drugs (restricted to sale only on a doctor's prescription) and over the counter and illicit drugs, hormones, peptides, mono and disaccharides, metabolites, pesticides, pollutants and other organic synthetic chemicals.

Drugs of interest include ethanol, alkaloids, such as morphine, codeine, heroin, dextramethorphan, and their derivatives and metabolites. Also included are ergotalkaloids such as LSD, steroid alkaloids, quinoline alkaloids, and others. Ethical drugs of interest include steroids, bile acids, digitoxin, diethylstilbesterol, ethynylestradiol and others.

Other drugs include barbiturates, such as phenobarbital, secobarbital, and others. Additionally, drugs such as amphetamines, catecholamines, serotonin, L-dopa, epinephrine, chlorpromazine, benzodiazepine, phenolthiazine, theophylline, caffeine, cannabis drugs such as cannabinol tetrahydrocannabinol, vitamins, prostaglandins, antibiotics such as penicillin and penicillin variants, cephalosporin and variants, chloromycetin, actinomycetin, and tetracycline, among others can be detected.

Nucleosides and nucleotides, fragments and derivatives thereof including ATP, AND, TMN, AZP, and others can be detected. Additionally, drugs including methadone, meprobamate, lidocaine, propanolol, antihistamines, anticholinergic drugs and others can be detected. Further, analytes specifically detected using the system of the present invention in clinical chemical analysis include glucose, cholesterol, triglycerides, uric acid, urea and other typical small molecule chemical analytes.

Antibodies useful in the detection zone of the test strip system of the present invention can be prepared by well known polyclonal and monoclonal antibody preparing techniques. Polyclonal antibodies can be raised conventionally in a variety of test animals including mice, rats, rabbits, horses, among others. Monoclonal antibodies can be prepared using well known techniques such as that disclosed by Kohler and Milstein, "Continuous Cultures of Fused Cells Secreting Antibody of Predetermined Specificity", Nature, Vol. 256, pp. 495–497, Aug. 7, 1975.

The present invention particularly lends itself to the clinical or at home detection of analytes and test fluids using oxidant enzymes requiring the presence of atmospheric oxygen to generate a unique signal in the presence of the test analyte. Particularly useful analysis include glucose detection using glucose oxidase, alcohol detection using alcohol oxidase, and cholesterol detection using cholesterol oxidase.

The test strip of the invention functions as follows. The overlay membrane treats the red blood cells with a crenating agent such as hypertonic sodium chloride so that the cells become rigid and crenated. This treatment of the cells could be carried out in solution, but this would not be convenient for a solid state system, such as the present invention. Normally erythrocytes have dimensions of 2×7 microns, but can wiggle through pores of 1 micron or less because of their flexibility. The detection membrane with pores of 1 micron or less holds back the crenated red blood cells while allowing molecules such as glucose, alcohols, etc. and aggregations such as cholesterol and its esters to pass through. These analytes undergo reaction within and on the back side of the detection membrane and an appropriate signal is generated.

The test strip of the invention can be employed in a variety of testing device formats. A detection zone for the detection of analytes can be formed on a carrier strip to which a volume of blood can be applied for the purpose of determining the presence of the target analyte in the blood serum. Alternatively, a "pH paper type strip device" can be used that can be unreeled from a strip dispenser. Another alternative is embodied in a mechanical device which combines a lance that can penetrate the skin to provide a blood sample, and a wicking cloth that contacts the blood sample and draws the sample to the dry strip device wherein the unique signal is produced with little or no RBC interference. Such devices can be visually read or can be read by instrumental methods and are disclosed in Garcia et al, U.S. Pat. Nos. 4,637,403 and 4,627,445.

Preferably the support carrier strip used in preparing the test strip of the invention which uses a detection system requiring the presence of atmospheric oxygen has a construction that promotes the transfer of oxygen from the atmosphere to the reaction site of the detection zone membrane. The dry test strip can be formed in such a way to promote atmospheric contact. One means comprises forming an aperture in the carrier support strip at the contact point between the strip and the detection zone membrane. Such an aperture can take the form of an oval, circular, or polygonal shaped cutout in the substrate strip. Alternatively, the aperture can comprise a highly oxygen permeable polymeric layer introduced into the carrier substrate opposite the color forming detection zone, through which oxygen can readily be transported for reaction. Preferably the dimensions of the aperture are smaller than the detection zone membrane but expose a significant portion of the area of the detection zone for oxygen transferred visual detection of the color change when analyte is present.

In another embodiment, the detection zone membrane can attached to the support strip using a construction design permitting the flow of atmospheric oxygen into the interface between the detection zone and the support strip. Such oxygen flow to the interface can be promoted by providing attachment means between the detection zone membrane and the underlying support such that a significant area volume between the detection zone and the support remains unoccupied providing access to atmospheric oxygen. Such a construction can be obtained by adhering the detection zone membrane to raised adhesive areas or to small areas of double sided adhesive tape leaving the majority of the reverse side of the detection zone to the contact of atmospheric oxygen.

The dry test strips of the invention can be manufactured by applying an overlaying adhesive on the support carrier having at least one aperture and then applying the detection zone membrane onto the support over the adhesive. An overlay membrane is then affixed to the support and is in overlying and continuous contact with the detection zone membrane. Preferably the aperture in the support strip is formed before the detection zone membrane is applied to the underlying support. Specific methods for manufacturing test strips of the invention are discussed below in the Examples.

A general method for using the diagnostic test strip of the invention comprising a support, a detection zone membrane, and an overlay membrane for the chemical or immunological assay of whole blood analytes comprises the steps of applying a sample of whole blood to the overlay membrane and analyzing a signal generated from the detection zone membrane to determine the presence of any given analyte.

A preferred immuno assay for the detection of analytes that can use the test system of the present invention is that disclosed in Liotta, U.S. Pat. No. 4,446,232. The test strip of the present invention comprising a Liotta type device has a matrix of three zones, a first labeled reagent zone, a second trapping zone, and a third detection zone for label detection. In a Liotta system the first labeled reagent zone contains a labeled antigen specific antibody or fragment thereof capable of bonding to a target analyte. The second trapping zone contains a boundary of immobilized antigen. The third detection zone contains a means for detecting the presence of the label on the antigen specific antibody or fragment thereof.

In the operation of the Liotta type device, a test fluid containing target analyte is applied to the matrix. The analyte in the fluid binds the antigen specific labeled antibody. The presence of the analyte on the binding sites of the antibody causes the analyte-antibody labeled complex to penetrate the matrix and pass through the trapping zone since the presence of analyte prevents the antibody and its label from becoming trapped by bound antigen. The protected antibody and label penetrate the third zone wherein the presence of the label is detected. In this way, the presence of analyte in the test fluid can produce a unique quantitative signal in the detection layer.

In the absence of analyte in the test fluid, no analyte can bond to the antigen specific labeled antibody. As the application of the test fluid causes the unbound labeled antibody to penetrate the second layer, bound antigen reacts with and traps the labeled antibody in the second layer preventing any of the label from penetrating and causing a detection signal in the third layer.

DETAILED DISCUSSION OF THE DRAWINGS

FIG. 1 is a planar view of a support 10 having reading site apertures 12 and an adhesive strip 18 overlying the reading sites 12 of support 10.

Figure 2:
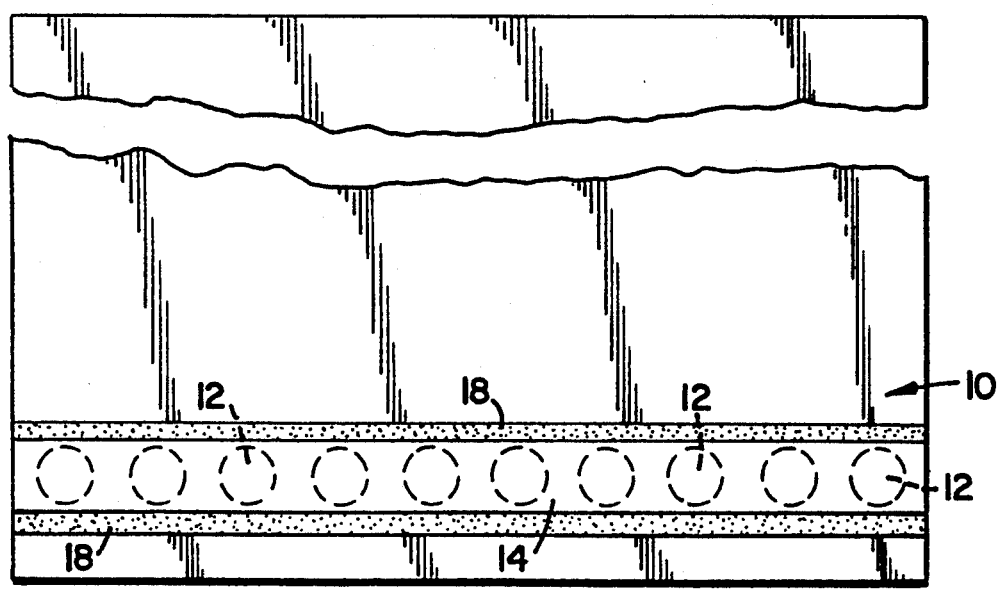
FIG. 2 depicts a planar view of the support having the detection zone membrane overlaying the reading sites.

FIG. 2 is a planar view of the support 10 having a detection zone membrane 14 overlaying the reading sites 12. The detection zone membrane 14 is attached to the support 10 by means of adhesive strip 18.

Figure 3:
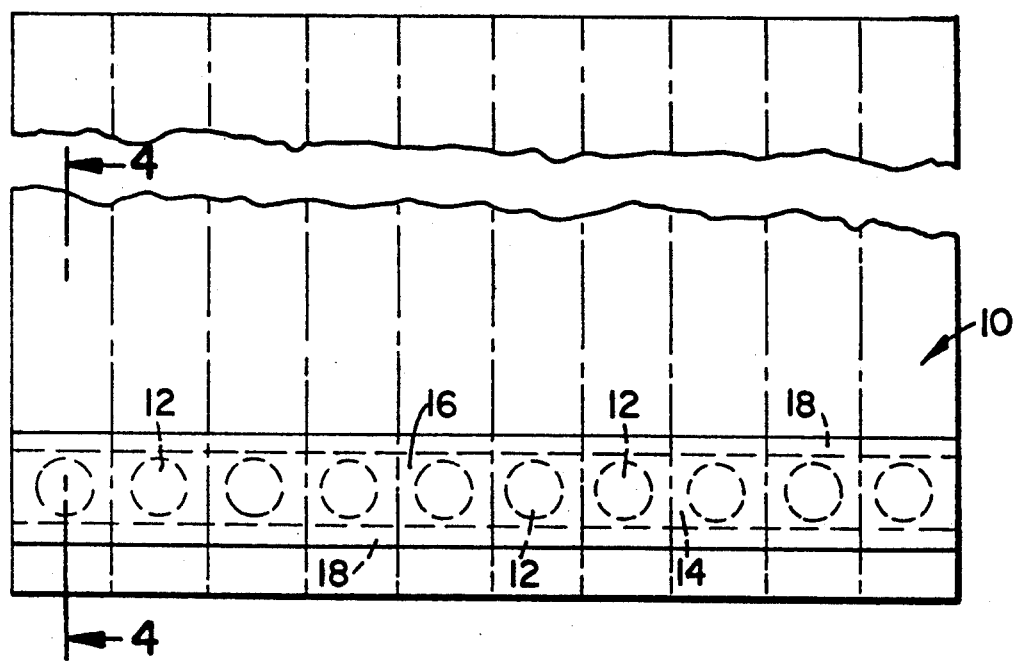
FIG. 3 depicts a planar view of the support used in the present invention with the overlay membrane affixed to the support and overlying the detection zone membrane according to a preferred embodiment of the invention.

FIG. 3 is a planar view of a preferred embodiment of the invention with support 10 having an overlay membrane 16 affixed to support 10. The overlay membrane 16 is in overlying and continuous contact with the detection zone membrane 14.

Figure 4:
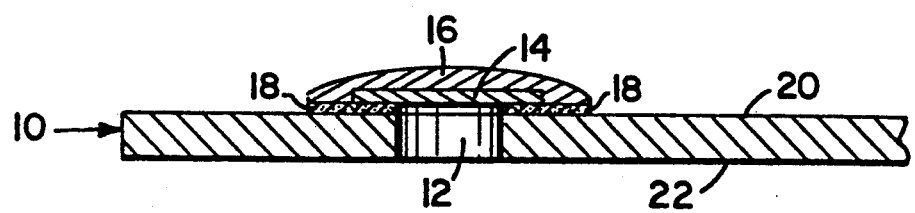
FIG. 4 depicts an enlarged cross-sectional view of the preferred embodiment of the invention shown in FIG. 3.

FIG. 4 is an enlarged cross-sectional view of the preferred embodiment of FIG. 3 showing the support 10 having aperture 12 over which the detection zone membrane 14 is placed. Overlay membrane 16 is affixed to support 10 by means of adhesive strip 18 and is in overlying and continuous contact with detection zone membrane 14. Side 20 of support 10 is the blood sample contact side and side 22 is the indicator reading side of the test strip.

WORKING EXAMPLES

The following working Examples disclose various test strips of the invention which were made and tested. The process for preparing the detection zone membrane of the test strips follows and was used in making the following test strip examples The process for preparing the detection zone membrane for the detection of cholesterol levels was carried out in three separate stages: (1) reaction of the membrane with polyallylamine; (2) impregnation with an aqueous mix; and (3) impregnation with an organic solvent mix. An Immunodyne membrane (Pall, Inc.) was incubated at ambient temperature in a mix of 10 ml of a buffer (0.1 M MES, 0.01 M Bicine, pH 6) and 3 mg of polyallylamine for 30 minutes. The membrane was then scraped to remove excess solution. The polyallylamine treated membrane was then incubated at ambient temperature in a milk mix of 20 ml of a buffer (same as above) and 1 g of instant, non-fat dry milk (Carnation) for 30 minutes, scraped to remove excess solution and then washed 3 times for 5 minutes with deionized water. The membrane was then dried for 10-20 minutes with forced air at 50° C. The dried treated membrane was then impregnated with an aqueous mix containing enzymes. The ingredients and respective amounts in the aqueous mix are listed in Table I.

TABLE I

| Ingredient | Amount |
| --- | --- |
| Aqueous Mix | |
| Buffer (0.1M MES, 0.01 Bicine, pH 6) | 2 ml |
| Heparin (1%) | 10 μl |
| Dextran (17000 mw) | 0.4 gms |
| Cholesterol Oxidase (Kodak) | 150 mg |
| Cholesterol Esterase (Kodak) | 40 mg |
| Peroxidase | 20 mg |
| Aerosol OT (American Cyanamide) | 240 μl |
| Methyl Vinyl Ether/Maleic Anhydride (10%, hydrolyzed, adjusted to pH 6) | 160 μl |
| Polyvinylpyrrolidone (10%) | 80 μl |
| Manganese Chloride | 5 mg |
| Organic Mix | |
| Toluene | 10 ml |
| Tetramethylbenzidine | 200 mg |
| Quinine | 0.5 mg |
| Aerosol OT | 100 mg |

The polyallylamine treated membrane was impregnated with the aqueous mix by laying the membrane on the surface of the mix until all the pores were filled. The membrane was then dried at 75° C. for 4 minutes. The membrane was then coated with an organic mix (see Table I) by drawing the membrane through the organic mix. The membrane was then dried at 75° C. for 4 minutes.

The overlay membrane was made from a hydrophilic HDC polypropylene membrane (Pall, Inc.) which was immersed in a 1 M sodium chloride solution containing 5 mg/L heparin until the membrane was saturated. The membrane was blotted and then dried at 75° C. for 10 minutes.

Double side adhesive was placed on a polystyrene support and holes were punched through the polystyrene and adhesive. The detection and overlay membranes were sequentially placed over the adhesive and rolled to insure intimate contact. The combination was then cut into sticks. This assembly of the test strip is shown in the drawings (FIGS. 1-3).

EXAMPLE 1

The test strip of Example 1 was formed using the above method.

EXAMPLE 2

The test strip of Example 2 was formed the same as Example 1, but without the crenating overlay membrane.

EXAMPLE 3

The test strip of Example 3 was made the same as Example 2, but omitted the polyallylamine treatment of the detection membrane.

TEST RESULTS

Using a sample of blood to test the exclusion of RBC, the strip of Example 1 provided the best results in that it had a total absence of red color and developed a clear green to blue color proportional to the cholesterol content of the blood. The strips of Example 2 allowed some hemoglobin from the cells through, giving a muddy colored reaction with cholesterol of the blood. The strips of Example 3 were completely hemoglobin stained and gave almost no reaction with cholesterol. The overlay membrane in combination with the polyallylamine treated detection membrane of Example 1 crenated and sequestered the red blood cells thereby allowing the cholesterol analyte to penetrate into the detection zone. However, it should be noted that adding sodium chloride to the aqueous mix used to make the detection zone membrane was not effective in crenating the cells.

EXAMPLES 4-12

The preceding analysis was run again to determine appropriate overlay membrane substitute materials. The detection zone membranes used on test strips 4-12 were made by the same method as used in making the test strips of Examples 1-3 above. The various overlay membranes were impregnated with a one molar NaCl solution and then dried at 75° C. for a period of 10 minutes. Various overlay membranes were then mounted on the detection zone membranes which had been mounted on a polystyrene support. The support was then cut into separate test strips. The various overlay membranes that were used are listed in Table II.

TABLE II

| Test Strip Ex. | Overlay Membrane | Pore Size |
|---|---|---|
| 4 | Polypropylene (HDC 1025b, Pall, Inc.) | — |
| 5 | Polypropylene (HDC 1026b, Pall, Inc.) | — |
| 6 | Polypropylene (HDC 1025a, Pall, Inc.) | — |
| 7 | Polypropylene (HDC 1026a, Pall Inc.) | — |
| 8 | Nylon (Biodyne A, Pall, Inc.) | 0.45 microns |
| 9 | Filter paper #54 hardened (Whatman) | |
| 10 | NO OVERLAY MEMBRANE (NaCl in organic mixture for coating detection membrane) | |
| 11 | Nylon (Biodyne A) | 1.2 microns |
| 12 | NO OVERLAY MEMBRANE (Control) | |

TEST RESULTS

Test strips 4, 5, 6, 7 and 10 all provided good analyte results from a serum sample. Test strip 9 would be able to provide adequate assay results if the two membranes retained better adhesion once contacted with the sample solution. Test strips 8 and 11 did not react at all.

Regarding the exclusion of RBC using a blood sample, all the strips were better than the control (strip 12), providing interference free results except for test strips 8, 10 and 11. Specifically, test strip 4 provided better results than test strips 5, 6, 7, 8 and 9.

In conclusion, the above working examples establish that sodium chloride incorporated in the overlay membrane is effective in shrinking and rigidifying RBC. Most of the above membranes worked as overlay layers when impregnated with NaCl to crenate RBC. However, Biodyne A having a pore size of 0.45 micron did not work at all, neither did Biodyne A having a 1.2 micron pore size.

Examples 13 and 14 are specific membrane overlays and reactive detection zone membranes prepared for solid state assays of glucose and cholesterol.

EXAMPLE 13

Glucose Detection

The membranes that were formulated for use on the glucose detection test strip of Example 13 were produced by a similar method as used in the previous Examples. The overlay membrane was formulated from an HDC polypropylene membrane (Pall, Inc.) which was treated with a 1 M NaCl containing 10 mg heparin per liter and then dried. A reactive membrane of Biodyne A (0.2 micron pore diameter—Pall, Inc.) was impregnated with an aqueous mix as shown in Table III. The membrane was then dried in a tunnel drier and passed through an organic mix (see Table III).

TABLE III

| Ingredient | Amount |
|---|---|
| Aqueous Mix | |
| Buffer (10 mm Citrate, pH 6) | 100 ml |
| Dextran (17000 MW) | 20 gms |
| Glucose Oxidase | 60000 units |
| Peroxidase | 90000 units |
| Methyl Vinyl Ether/Maleic Anhydride (hydrolyzed) | 0.8 gms |
| Polyvinylpyrrolidone 40 | 0.4 gms |
| Organic Mix | |
| Methanol | 100 ml |
| Gantrez S95 | 0.3 gms |
| Tartrazine | 0.03 gms |
| o-Tolidine | 0.5 gms |
| Tetramethylbenzidine | 0.2 gms |

The membrane was dried again in the tunnel dryer. The reactive membrane was then cut into ¼ inch strips and attached to a polystyrene backing with a double sided adhesive (holes were punched through the backing and adhesive first.) The adhesive extended slightly beyond the width of the membrane strips. The treated overlay membrane was then cut into strips slightly wider than the reactive membrane strips. The overlay membrane strip was placed over the reactive membrane strip so that the overlay strip was attached to the backing with the above adhesive. This combination was then cut into single sticks.

TEST RESULTS

When blood was placed on the overlay membrane of the sticks, the reverse side of the reactive membrane turned from green to blue to black as the glucose level of the blood increased. No blood or hemoglobin color appeared on the reverse side (reading side) of the reactive detection zone membrane.

EXAMPLE 14

Cholesterol Detection

The test strip of Example 14 was made by the following method. The overlay membrane was formulated from an HDC polypropylene membrane (Pall, Inc.) which was treated with 1 M NaCl containing 10 mg heparin per liter and then dried. The reactive membrane Immunodyne (Pall, Inc., 1.2 micron diameter pore) was treated with polyallylamine hydrochloride (30 mg/100 ml) in a pH 6 buffer of 0.1 M morpholinoethanesulfonic acid (MES) and 0.01 M bis-dihydroxyethylglycine (Bicine). The membrane was washed with deionized water and dried. The membrane was then treated with Carnation fat-free dried milk (0.5% in the pH 6 buffer), dried, washed with deionized water and dried again.

The treated membrane was then impregnated with an aqueous mix as shown in Table IV.

TABLE IV

| Aqueous Mix | |
|---|---|
| Ingredient | Amount |
| Buffer (pH 6, 0.1M MES, 0.01 Bicine) | 4 ml |
| Cholesterol Oxidase (Kodak) | 500 units |
| Cholesterol Esterase (Kodak) | 1000 units |
| Heparin (1%) | 20 µl |
| Peroxidase | 1000 units |
| Dextran (17000 MW) | 800 mg |
| Aerosol OT (American Cyanamid) (7%) | 480 µl |
| Methyl Vinyl Ether/Maleic Anhydrided (hydrolyzed, 10%) | 320 µl |
| Polyvinylpyrrolidone (10%) | 160 µl |

In preparing the above mixture, phosphate was removed from the cholesterol oxidase and esterase by dissolving the two enzymes in 2 ml of the MES-Bicine buffer, placing the solution on a Sephadex G-25 column (Pharmacia PD 10) and eluting with buffer until a volume of 4 ml was collected. The other ingredients were then added and mixed. The impregnated membrane was dried and then treated with a saturated indicator solution of tetramethylbenzidine in toluene and dried.

The reactive detection zone membrane and the overlay membrane were placed on a polystyrene backing with a double sided adhesive as described in Example 13 and then cut into sticks.

TEST RESULTS

When the sticks were contacted with blood, they turned from green to blue depending on the level of cholesterol and its esters. The reactivity of the sticks may be varied by including inhibitors or other indicators in the aqueous toluene mixture used in the detection zone membrane. By omitting esterase from the composition, the same system can be used to determine free cholesterol.

The same system for screening out erythrocytes while allowing cholesterol and its esters through can be combined with the teaching of Liotta described above to determine low density lipoproteins and high density lipoproteins using the antisera to the apolipoproteins.

The purpose of the heparin in the overlay treatments of Examples 13 and 14 is to prevent the hemolysis of erythrocytes caused by stretching of the cells in contact with the membrane.

While the invention has been described and fully explained in the detailed description of the specification and preferred embodiments, many embodiments of the invention can be made without departing from the spirit and scope of the invention.

We claim as our invention:

1. A diagnostic test strip for the chemical or immunological assay of whole blood analytes comprising:
   (a) a support having at least one aperture therein;
   (b) a porous detection zone membrane affixed to said support and overlying said aperture; and
   (c) an overlay membrane affixed to said support and in overlying and continuous contact with said detection zone membrane, said overlay membrane comprising an effective red blood cell excluding amount of a crenating agent for the exclusion of whole red blood cells from the pores of said detection zone membrane;
   wherein said red blood cells are crenated and made rigid in passing through said overlay membrane to the surface of said detection zone membrane and are thereby excluded by the pores of said detection zone membrane from entering therein.

2. The test strip of claim 1 wherein said crenating agent is an inorganic or organic salt.

3. The test strip of claim 2 wherein said crenating agent is an alkali or alkali earth metal salt of a halogen.

4. The test strip of claim 3 wherein said crenating agent is sodium chloride, potassium chloride, or lithium chloride.

5. The test strip of claim 1 wherein said overlay membrane comprises a synthetic polymeric material and has a thickness of about 0.1 to 1,000 microns.

6. The test strip of claim 5 wherein said overlay membrane is polypropylene, polyvinyl chloride, or polyester.

7. The test strip of claim 1 wherein said detection zone membrane is a natural or synthetic polymer.

8. The test strip of claim 7 wherein said detection zone membrane comprises a nylon sheet cast on a polyester layer.

9. The test strip of claim 1 wherein said porous detection zone membrane has pores ranging in size from about 0.2 to 3 microns.

10. The test strip of claim 1 wherein said detection zone membrane comprises an activated colorimetric indicator for determining a select analyte constituent in whole blood.

11. The test strip of claim 1 wherein said detection zone membrane additionally comprises analyte reactive precursors that react with the whole blood analyte to provide a constituent determinable by said detection zone membrane.

12. The test strip of claim 11 wherein said analyte reactive precursors comprise cholesterol ester hydrolase and cholesterol oxidase.

13. The test strip of claim 11 wherein said analyte reactive precursors comprise glucose oxidase and peroxidase.

14. The test strip of claim 1 wherein said support is a natural or synthetic material.

15. The test strip of claim 14 wherein said support is polystyrene, polyethylene, polypropylene, or polyvinyl chloride.

16. A method of using a diagnostic test strip for the chemical or immunological assay of whole blood analytes comprising a support having at least one aperture therein, a porous detection zone membrane affixed to said support and overlying said aperture, and an overlay membrane affixed to said support and in overlying and continuous contact with said detection zone membrane, said overlay membrane comprising an effective amount of a crenating agent for the exclusion of whole red blood cells from the pores of said detection zone membrane, said method comprising the steps of:
   (a) applying a sample of whole blood to said overlay membrane, wherein the red blood cells are crenated and made rigid in passing through said overlay membrane to the surface of said detection zone membrane and are thereby excluded by the pores of said detection zone membrane from entering therein; and
   (b) analyzing a signal generated from said detection zone membrane to determine the presence of any given analyte.

17. A diagnostic test strip for the chemical or immunological assay of whole blood analytes comprising:

(a) a support which is a natural or synthetic material, said support having at least one viewing aperture therein;

(b) a porous detection zone membrane affixed to said support and overlaying said aperture, said detection zone membrane having analyte reactive precursors that react with whole blood analytes to provide a constituent determinable by said detection zone membrane, said reactive precursors comprising cholesterol ester hydrolase and cholesterol oxidase; and (c) an overlay membrane affixed to said support and in overlying and continuous contact with said detection zone membrane, said overlay membrane selected from the group consisting of polypropylene, polyvinyl chloride, and polyester membranes, said overlay membrane having a crenating agent for the exclusion of whole red blood cells from the pores of said detection zone membrane, wherein said crenating agent is an organic or inorganic salt; wherein said red blood cells are crenated and made rigid in passing through said overlay membrane to the surface of said detection zone membrane and are thereby excluded by the pores of said detection zone membrane from entering therein.

18. A method of using the diagnostic test strip of claim 17 for the chemical or immunological assay of whole blood analytes comprising the steps of:

(a) applying a sample of whole blood to said overlay membrane, wherein said red blood cells are crenated and made rigid in passing through said overlay membrane to the surface of said detection zone membrane and are thereby excluded by the pores of said detection zone membrane from entering therein; and (b) analyzing a signal generated from said detection zone membrane to determine the presence of any given analyte.

19. A diagnostic test strip for the chemical or immunological assay of whole blood analytes comprising:

(a) a support which is a natural or synthetic material, said support having at least one viewing aperture therein;

(b) a porous detection zone membrane affixed to said support and overlying said aperture, said detection zone membrane having analyte reactive precursors that react with whole blood analytes to provide a constituent determinable by said detection zone membrane, said reactive precursors comprising glucose oxidase and peroxidase; and (c) an overlay membrane affixed to said support and in overlying and continuous contact with said detection zone membrane, said overlay membrane selected from the group consisting of polypropylene, polyvinyl chloride and polyester membranes, said overlay membrane having a crenating agent for the exclusion of whole red blood cells from the pores of the detection zone membrane, wherein said crenating agent is an organic or inorganic salt; wherein said red blood cells are crenated and made rigid in passing through said overlay membrane to the surface of said detection zone membrane and are thereby excluded by the pores of said detection zone membrane from entering therein.

20. A method of using the diagnostic test strip of claim 19 for the chemical or immunological assay of whole blood analytes comprising the steps of:

(a) applying a sample of whole blood to said overlay membrane, wherein said red blood cells are crenated and made rigid in passing through said overlay membrane to the surface of said detection zone membrane and are thereby excluded by the pores of said detection zone membrane from entering therein; and (b) analyzing a signal generated from said detection zone membrane to determine the presence of any given analyte.

* * * * *